US012778690B2

(12) United States Patent
Hage

(10) Patent No.: US 12,778,690 B2
(45) Date of Patent: Nov. 3, 2026

(54) SYSTEM AND METHOD FOR REDUCING TOOL VIBRATION AT A VARIABLE STIFFNESS END EFFECTOR OF A SURGICAL SYSTEM

(71) Applicant: Medtronic Navigation, Inc., Louisville, CO (US)

(72) Inventor: Richard Todd Hage, Castle Rock, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 184 days.

(21) Appl. No.: 18/608,386

(22) Filed: Mar. 18, 2024

(65) Prior Publication Data

US 2024/0359338 A1 Oct. 31, 2024

Related U.S. Application Data

(60) Provisional application No. 63/462,301, filed on Apr. 27, 2023, provisional application No. 63/462,330, filed on Apr. 27, 2023.

(51) Int. Cl.
*A61B 17/00* (2006.01)
*A61B 34/30* (2016.01)
(Continued)

(52) U.S. Cl.
CPC .............. *A61B 34/30* (2016.02); *A61B 17/00* (2013.01); *B25J 9/1664* (2013.01);
(Continued)

(58) Field of Classification Search
CPC ... A61B 90/50; A61B 34/30; A61B 2090/508; A61B 2034/305; B25J 17/0208
See application file for complete search history.

(56) References Cited

U.S. PATENT DOCUMENTS 4,627,169 A * 12/1986 Zafred .................... B23Q 1/36 33/642
4,921,393 A * 5/1990 Andeen .................... B25J 9/104 414/744.2
(Continued)

FOREIGN PATENT DOCUMENTS

CN 113288439 B 5/2022
EP 3932359 A1 1/2022

OTHER PUBLICATIONS

International Search Report and Written Opinion for related International Application No. PCT/IB2024/054080; dated: Oct. 18, 2024; 13 pages.
(Continued)

*Primary Examiner* — Stephen Holwerda
(74) *Attorney, Agent, or Firm* — Harrity & Harrity, LLP

(57) ABSTRACT

A variable stiffness end effector assembly for a medical robotic guidance system includes an end effector support and a tool insertion device disposed within and spaced apart from the end effector support. The assembly further includes a coupler coupling the tool insertion device within the end effector support. The coupler includes a first mode wherein the tool insertion device is rigidly coupled within the end effector support and second mode wherein the tool insertion device is compliantly coupled within the end effector support.

33 Claims, 15 Drawing Sheets

(51) Int. Cl.
*B25J 9/16* (2006.01)
*B25J 15/00* (2006.01)

(52) U.S. Cl.
CPC . *B25J 15/0061* (2013.01); *A61B 2017/00477* (2013.01); *A61B 2034/301* (2016.02)

(56) References Cited

U.S. PATENT DOCUMENTS

| | | | | |
|---|---|---|---|---|
| 5,125,759 | A * | 6/1992 | Chun | B25J 17/0208 403/291 |
| 5,592,939 | A | 1/1997 | Martinelli | |
| 5,820,623 | A | 10/1998 | Ng | |
| 5,909,941 | A * | 6/1999 | Cheng | B25J 17/0208 33/644 |
| 5,913,820 | A | 6/1999 | Bladen et al. | |
| 5,983,126 | A | 11/1999 | Wittkampf | |
| 6,246,200 | B1 | 6/2001 | Blumenkranz et al. | |
| 6,325,808 | B1 | 12/2001 | Bernard et al. | |
| 6,474,341 | B1 | 11/2002 | Hunter et al. | |
| 6,940,941 | B2 | 9/2005 | Gregerson et al. | |
| 7,001,045 | B2 | 2/2006 | Gregerson et al. | |
| 7,106,825 | B2 | 9/2006 | Gregerson et al. | |
| 7,108,421 | B2 | 9/2006 | Gregerson et al. | |
| 7,188,998 | B2 | 3/2007 | Gregerson et al. | |
| 7,751,865 | B2 | 7/2010 | Jascob et al. | |
| 8,175,681 | B2 | 5/2012 | Hartmann et al. | |
| 8,498,744 | B2 | 7/2013 | Odermatt et al. | |
| 8,503,745 | B2 | 8/2013 | Simon et al. | |
| 8,737,708 | B2 | 5/2014 | Hartmann et al. | |
| 8,961,537 | B2 | 2/2015 | Leung et al. | |
| 9,084,613 | B2 | 7/2015 | Qutub | |
| 9,333,039 | B2 | 5/2016 | Kuchenbecker et al. | |
| 9,737,235 | B2 | 8/2017 | Hartmann | |
| 9,901,411 | B2 | 2/2018 | Gombert et al. | |
| 10,624,709 | B2 | 4/2020 | Remm | |
| 11,135,025 | B2 | 10/2021 | Snyder et al. | |
| 11,602,474 | B2 | 3/2023 | Timm et al. | |
| 12,053,252 | B2 | 8/2024 | Thompson et al. | |
| 12,133,699 | B2 | 11/2024 | Crawford et al. | |
| 12,446,981 | B2 | 10/2025 | Crawford et al. | |
| 2002/0111634 | A1* | 8/2002 | Stoianovici | A61B 90/50 606/129 |
| 2009/0062813 | A1* | 3/2009 | Prisco | A61B 34/37 606/130 |
| 2010/0009825 | A1* | 1/2010 | Norton | B25J 17/0208 901/41 |
| 2012/0330198 | A1* | 12/2012 | Patoglu | A61H 1/0281 601/33 |
| 2015/0216604 | A1* | 8/2015 | Piccin | B25J 15/12 606/130 |
| 2016/0310221 | A1* | 10/2016 | Bar | A61B 90/06 |
| 2019/0009391 | A1* | 1/2019 | Sato | B25B 11/02 |
| 2019/0084056 | A1* | 3/2019 | Sweet | B23B 51/102 |
| 2019/0117320 | A1 | 4/2019 | Shoham et al. | |
| 2019/0117321 | A1 | 4/2019 | Park et al. | |
| 2021/0007813 | A1 | 1/2021 | Yates et al. | |
| 2021/0052338 | A1 | 2/2021 | Hill et al. | |
| 2021/0052340 | A1* | 2/2021 | Rabindran | A61B 17/2909 |
| 2022/0022981 | A1 | 1/2022 | Shoham et al. | |
| 2022/0061934 | A1* | 3/2022 | Sen | A61B 34/30 |
| 2022/0125535 | A1 | 4/2022 | Janna et al. | |
| 2022/0160440 | A1 | 5/2022 | Jaramaz et al. | |
| 2022/0218421 | A1 | 7/2022 | Junio et al. | |
| 2023/0390001 | A1* | 12/2023 | Bowling | A61B 34/10 |

OTHER PUBLICATIONS

U.S. Appl. No. 18/608,347, filed Mar. 18, 2024, Richard Todd Hage.
U.S. Appl. No. 63/462,301, filed Apr. 27, 2023, Richard Todd Hage.
U.S. Appl. No. 63/462,330, filed Apr. 27, 2023, Richard Todd Hage.

* cited by examiner

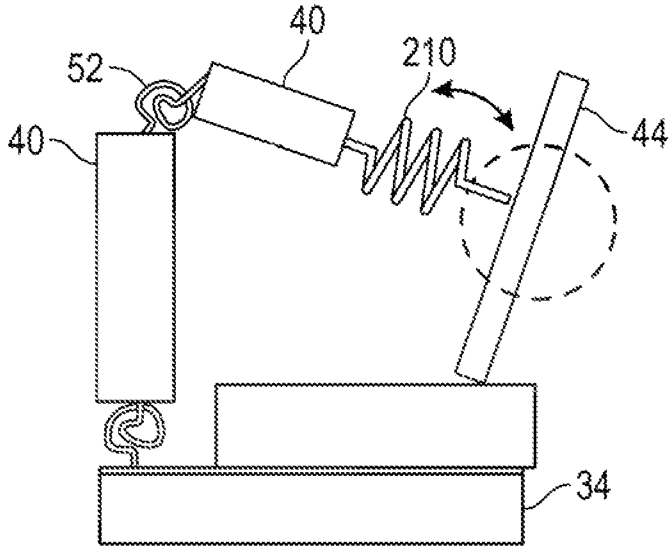
FIG. 2A
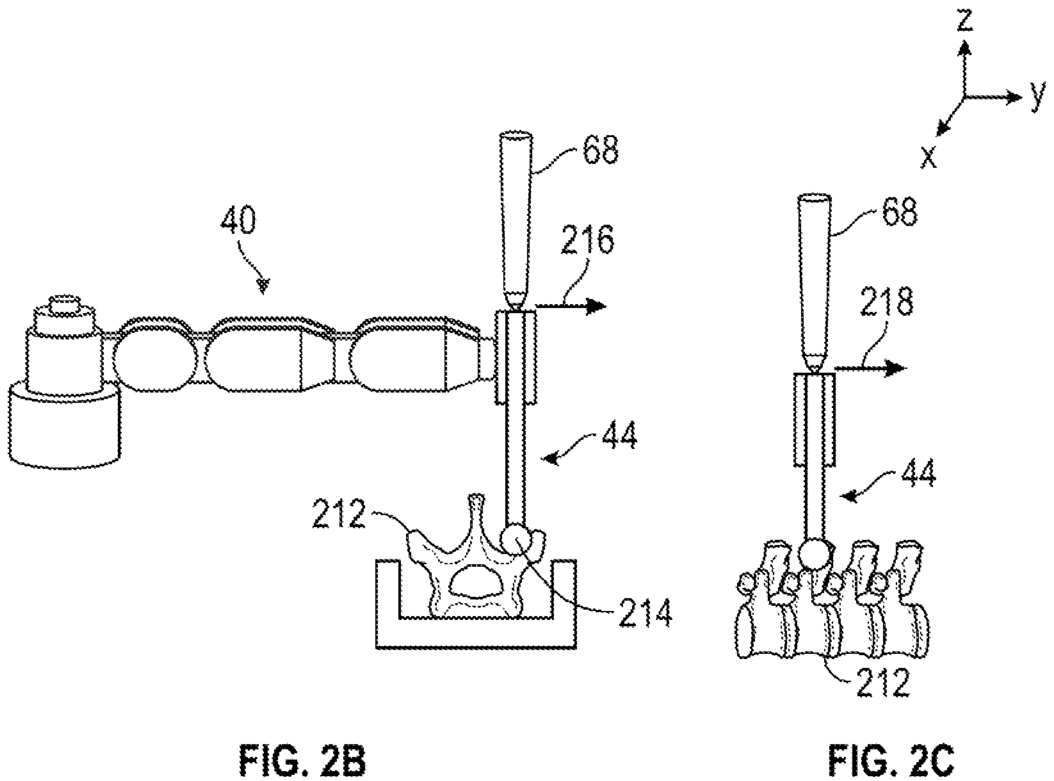
FIG. 2B
FIG. 2C

SYSTEM AND METHOD FOR REDUCING TOOL VIBRATION AT A VARIABLE STIFFNESS END EFFECTOR OF A SURGICAL SYSTEM

CROSS-REFERENCE TO RELATED APPLICATIONS

This application claims the benefit of and priority to U.S. Provisional Patent Application No. 63/462,330 filed Apr. 27, 2023 and U.S. Provisional Patent Application No. 63/462,301 filed Apr. 27, 2023, and the disclosures of each of the above-identified applications are hereby incorporated by reference in their entirety.

FIELD

The subject disclosure is related generally to a robotic surgical system, and particularly to a system for decoupling vibrations from an end effector at a robotic arm.

BACKGROUND

This section provides background information related to the present disclosure which is not necessarily prior art.

An instrument can be navigated relative to a subject for performing various procedures. For example, the subject can include a patient on which a surgical procedure is being performed. During a surgical procedure, an instrument can be tracked in an object or subject space. The location of the instrument that is tracked can be displayed on a display device relative to an image of the patient.

The position of the patient can be determined with a tracking system. Generally, a patient is registered to the image, via tracking an instrument relative to the patient to generate a translation map between the subject or object space (e.g., patient space) and the image space.

After registration, the position of the instrument can be appropriately displayed on the display device while tracking the instrument. The position of the instrument relative to the subject can be displayed as a graphical representation, sometimes referred to as an icon on the display device.

The instrument in guided surgery, particularly in spinal surgery, has a particular challenge for holding the position in a rigid system. A tool such as drill is used with a guide at end effector at the end of a robotic arm. Typically, a robotic arm has high rigidity relative to the patient and relative to the robot arm. The high rigidity may result in undesired system dynamics. The system dynamics may occur in natural vibrations at a high frequency due to the high stiffness in the system.

SUMMARY

This section provides a general summary of the disclosure and is not a comprehensive disclosure of its full scope or all of its features.

The present system allows is a variable stiffness end effector that allows quick decoupling of a rigid mechanism and coupling using a compliant mechanism of the parts of the end effector support. In particular, the present disclosure allows the end effector support to be quickly decoupled from the tool insertion device located within the end effector support. This allows the natural frequency of the system to rapidly decrease and prevent natural frequency vibrations.

In one aspect of the disclosure, a variable stiffness end effector assembly for a medical robotic guidance system includes an end effector support and a tool insertion device disposed within and spaced apart from the end effector support. The assembly further includes a coupler coupling the tool insertion device within the end effector support. The coupler includes a first mode wherein the tool insertion device is rigidly coupled within the end effector support and second mode wherein the tool insertion device is compliantly coupled within the end effector support.

In another aspect of the disclosure, a system has a robotic arm with a variable stiffness end effector assembly comprising a tool insertion device disposed within the end effector support and coupled thereto with a coupler. The coupler comprises a first mode wherein the tool insertion device is rigidly coupled within the end effector support and second mode wherein the tool insertion device is compliantly coupled within the end effector support. A robotic control system is configured to control movement of the end effector support assembly. An input system is configured to receive input from a user and send a signal to the robotic control system to move the end effector support relative to a subject.

According to various embodiments, the end effector assembly may be moved relative to a subject, such as by a user and/or with a robotic system. The robotic system may include any appropriate robotic system, such as a Mazor X™ Robotic Guidance System, sold by Mazor Robotics Ltd. having a place of business in Israel and/or Medtronic, Inc. having a place of business in Minnesota, USA and/or as disclosed in U.S. Pat. No. 11,135,025, incorporated herein by reference.

The tracking or navigation system may include the end effector assembly, may also be used in various techniques and include an imaging system or following selected portions in a procedure. For example, the end effector assembly may be associated with the robotic system. The robotic system may move the end effector in a selected manner during the procedure. During the procedure, the end effector assembly may be moved based upon predetermined characteristics to follow for a selected portion during the procedure, such as during drilling for implanting certain implantable devices such as a spinal implant.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is a model of a robotic arm and end effector assembly attached thereto.

FIGS. 2B and 2C are respective front and side views of a robotic arm having straight vertical forces and Shanz forces parallel with the spine.

FIGS. 2H and 21 are respective front and side views of a robotic arm having caudal tilt forces and Shanz forces parallel with the spine.

Corresponding reference numerals indicate corresponding parts throughout the several views of the drawings.

DETAILED DESCRIPTION

Figure 1:
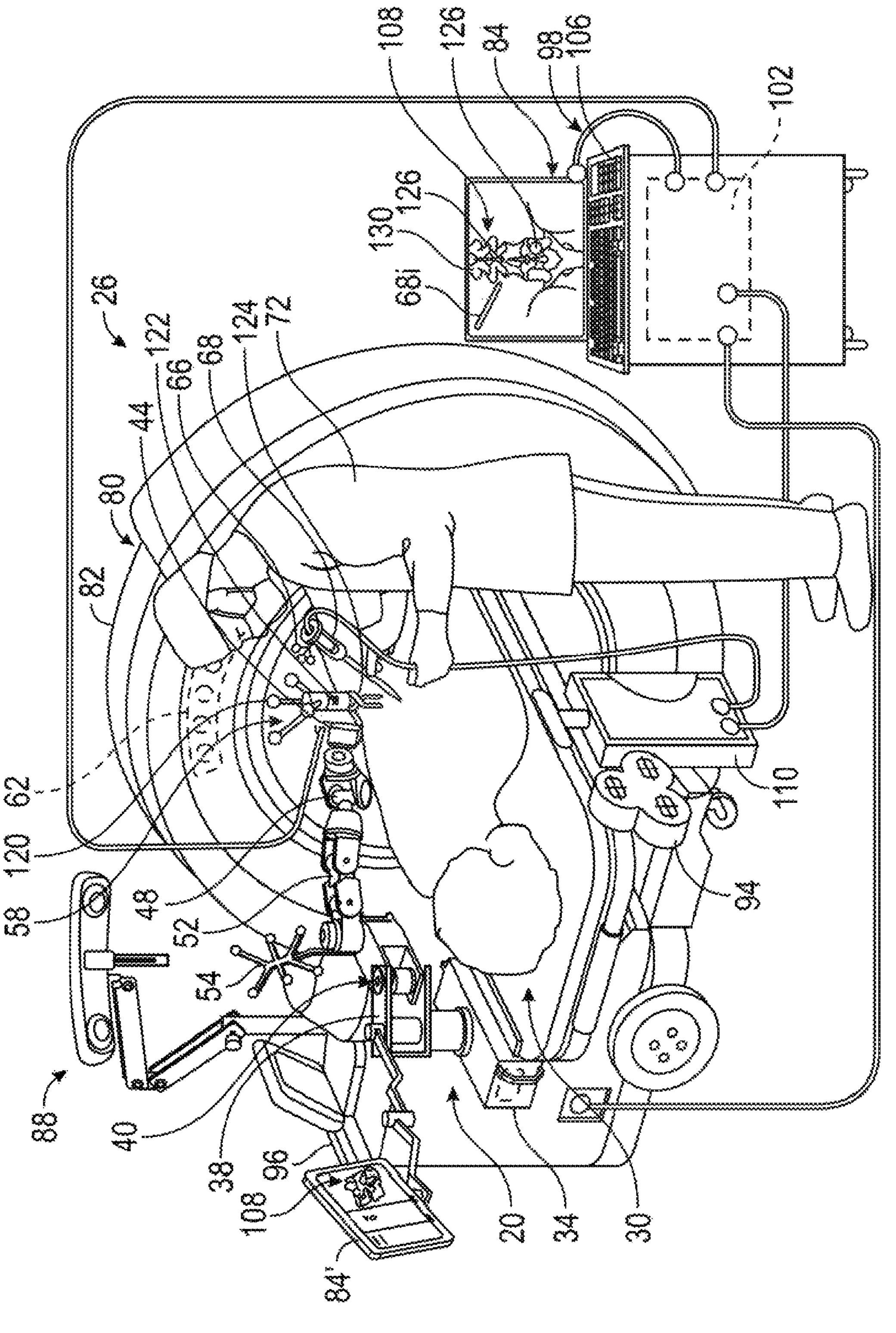
FIG. 1 is diagrammatic view illustrating an overview of a robotic system and a navigation system, according to various embodiments.

Example embodiments will now be described more fully with reference to the accompanying drawings.

The subject disclosure is directed to an exemplary embodiment of a surgical procedure on a subject, such as a human patient. It is understood, however, that the system and methods described herein are merely exemplary and not intended to limit the scope of the claims included herein. In various embodiments, it is understood, that the systems and methods may be incorporated into and/or used on non-animate objects. The systems may be used to, for example, to register coordinate systems between two systems for use on manufacturing systems, maintenance systems, and the like. For example, automotive assembly may use one or more robotic systems including individual coordinate systems that may be registered together for coordinated or consorted actions. Accordingly, the exemplary illustration of a surgical procedure herein is not intended to limit the scope of the appended claims.

Discussed herein, according to various embodiments, are processes and systems for allowing the use of and navigation and registration between various coordinate systems, including robotic coordinate systems. In various embodiments, a first coordinate system may be registered to a second coordinate system, such as a robotic coordinate system to an image coordinate system or space. A navigation space or coordinate system may then be registered to the robotic or first coordinate system and, therefore, be registered to the image coordinate system without being separately or independently registered to the image space. Similarly, the navigation space or coordinate system may be registered to the image coordinate system or space directly or independently. The robotic or first coordinate system may then be registered to the navigation space and, therefore, be registered to the image coordinate system or space without being separately or independently registered to the image space.

In various embodiments, the different systems used relative to the subject may include different coordinate systems (e.g., locating systems). For example, a robotic system may be moved relative to a subject that includes a robotic coordinate system. The robot may be fixed, including removably fixed, at a position relative to the subject. Thus, movement of a portion of the robot relative to the base of the robot (i.e., the fixed portion of the robot) may be known due to various features of the robot. For example, encoders (e.g., optical encoders, potentiometer encoders, or the like) may be used to determine movement or amount of movement of various joints (e.g., pivots) of a robot. A position of an end effector assembly (e.g., a terminal end) of the robot may be known relative to the base of the robot. Given a known position of the subject relative to the base and the known position of the base relative to the subject, the position of the end effector assembly relative to the subject may be known during movement of a robot and/or during a stationary period of the end effector assembly. Thus, the robot may define a coordinate system relative to the subject.

Various other portions may also be tracked relative to the subject. For example, a tracking system may be incorporated into a navigation system that includes one or more instruments that may be tracked relative to the subject. The navigation system may include one or more tracking systems that track various portions, such as tracking devices, associated with instruments. The tracking system may include a localizer that is configured to determine the position of the tracking device in a navigation system coordinate system. Determination of the navigation system coordinate system may include those described at various references including U.S. Pat. Nos. 8,737,708; 9,737,235; 8,503,745; and 8,175,681; all incorporated herein by reference. In particular, a localizer may be able to track an object within a volume relative to the subject. The navigation volume, in which a device, may be tracked may include or be referred to as the navigation coordinate system or navigation space. A determination or correlation between the two coordinate systems may allow for or also be referred to as a registration between two coordinate systems.

In various embodiments, the first coordinate system, which may be a robotic coordinate system, may be registered to a second coordinate system, which may be a navigation coordinate system. Accordingly, coordinates in one coordinate system may then be transformed to a different or second coordinate system due to a registration. Registration may allow for the use of two coordinate systems and/or the switching between two coordinate systems. For example, during a procedure, a first coordinate system may be used for a first portion or a selected portion of a procedure and a second coordinate system may be used during a second portion of a procedure. Further, two coordinate systems may be used to perform or track a single portion of a procedure, such as for verification and/or collection of additional information.

Furthermore, images may be acquired of selected portions of a subject. The images may be displayed for viewing by a user, such as a surgeon. The images may have superimposed on a portion of the image a graphical representation of a tracked portion or member, such as an instrument. According to various embodiments, the graphical representation may be superimposed on the image at an appropriate position due to registration of an image space (also referred to as an image coordinate system) to a subject space. A method to register a subject space defined by a subject to an image space may include those disclosed in U.S. Pat. Nos. 8,737,708; 9,737,235; 8,503,745; and 8,175,681; all incorporated herein by reference.

During a selected procedure, the first coordinate system may be registered to the subject space or subject coordinate system due to a selected procedure, such as imaging of the subject. In various embodiments, the first coordinate system may be registered to the subject by imaging the subject with a fiducial portion that is fixed relative to the first member or system, such as the robotic system. The known position of the fiducial relative to the robotic system may be used to register the subject space relative to the robotic system due to the image of the subject including the fiducial portion. Thus, the position of the robotic system or a portion thereof, such as the end effector assembly, may be known or determined relative to the subject. Due to registration of a second coordinate system to the robotic coordinate system may allow for tracking of additional elements not fixed to the robot relative to a position determined or tracked by the robot.

The tracking of an instrument during a procedure, such as a surgical or operative procedure, allows for navigation of a procedure. When image data is used to define an image space it can be correlated or registered to a physical space defined by a subject, such as a patient. According to various embodiments, therefore, the patient defines a patient space in which an instrument can be tracked and navigated. The image space defined by the image data can be registered to the patient space defined by the patient. The registration can occur with the use of fiducials that can be identified in the image data and in the patient space.

FIG. 1 is a diagrammatic view illustrating an overview of a procedure room or arena. In various embodiments, the procedure room may include a surgical suite in which may be placed a medical robotic system 20 and a navigation system 26 that can be used for various procedures. The robotic system 20 may include a Mazor X™ robotic guidance system, sold by Medtronic, Inc. The robotic system 20 may be used to assist in guiding a selected instrument, such as drills, screws, etc. relative to a subject 30. The robotic system 20 may include a mount 34 that fixes a portion, such as a robotic base 38, relative to the subject 30. The robotic system 20 may include one or more arms 40 that are moveable or pivotable relative to the subject 30, such as including an end effector assembly 44. The end effector assembly 44 may be any appropriate portion, such as an elongated tube, guide, or passage member. The end effector 44 may be moved relative to the base 38 with one or more motors. The position of the end effector assembly 44 may be known or determined relative to the base 38 with one or more encoders at one or more joints, such as a wrist joint 48 and/or an elbow joint 52 of the robotic system 20.

The navigation system 26 can be used to track the location of one or more tracking devices, tracking devices may include a robot tracking device 54, a subject tracking device 58, an imaging system tracking device 62, and/or a tool tracking device 66. A tool 68 or moveable member may be any appropriate tool such as a drill, forceps, or other tool operated by a user 72. The tool 68 may also include an implant, such as a spinal implant or orthopedic implant. It should further be noted that the navigation system 26 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure.

An additional or alternative, imaging system 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-arm® imaging device sold by Medtronic Navigation, Inc. having a place of business in Louisville, Colorado, USA. The imaging device 80 may have a generally annular gantry housing 82 in which an image capturing portion is moveably placed. The imaging device 80 can include those disclosed in U.S. Pat. Nos. 7,188,998; 7,108,421; 7,106,825; 7,001,045; and 6,940,941; all of which are incorporated herein by reference, or any appropriate portions thereof. It is further appreciated that the imaging device 80 may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

The position of the imaging system 33, 80, and/or portions therein such as the image capturing portion, can be precisely known relative to any other portion of the imaging device 33, 80. The imaging device 33, 80, according to various embodiments, can know and/or recall precise coordinates relative to a fixed or selected coordinate system. For example, the robotic system 20 may know or determine its position and position the effector assembly 44 at a selected pose. Similarly, the imaging system 80 may also position the imaging portions at a selected pose. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

Herein, reference to the imaging system 80 may refer to any appropriate imaging system, unless stated otherwise.

The imaging device 80 can be tracked with a tracking device 62. Also, a tracking device 81 can be associated directly with the effector assembly 44. The effector assembly 44 may, therefore, be directly tracked with a navigation system as discussed herein. In addition or alternatively, the effector assembly 44 may be positioned and tracked with the robotic system 20. Regardless, image data defining an image space acquired of the patient 30 can, according to various embodiments, be registered (e.g., manually, inherently, or automatically) relative to an object space. The object space can be the space defined by a patient 30 in the navigation system 26.

The patient 30 can also be tracked as the patient moves with a patient tracking device, DRF, or tracker 58. Alternatively, or in addition thereto, the patient 30 may be fixed within navigation space defined by the navigation system 26 to allow for registration. As discussed further herein, registration of the image space to the patient space or subject space allows for navigation of the instrument 68 with the image data. When navigating the instrument 68, a position of the instrument 68 can be illustrated relative to image data acquired of the patient 30 on a display device 84. An additional and/or alternative display device 84' may also be present to display an image. Various tracking systems, such as one including an optical localizer 88 or an electromagnetic (EM) localizer 92 can be used to track the instrument 68.

More than one tracking system can be used to track the instrument 68 in the navigation system 26. According to various embodiments, these can include an electromagnetic tracking (EM) system having the EM localizer 94 and/or an optical tracking system having the optical localizer 88. Either or both of the tracking systems can be used to track selected tracking devices, as discussed herein. It will be understood, unless discussed otherwise, that a tracking device can be a portion trackable with a selected tracking system. A tracking device need not refer to the entire member or structure to which the tracking device is affixed or associated.

The position of the patient 30 relative to the imaging device 33 can be determined by the navigation system 26. The position of the imaging system 33 may be determined, as discussed herein. The patient 30 can be tracked with the dynamic reference frame 58, as discussed further herein. Accordingly, the position of the patient 30 relative to the imaging device 33 can be determined.

Image data acquired from the imaging system 33, or any appropriate imaging system, can be acquired at and/or forwarded from an image device controller 96, that may include a processor module, to the navigation computer and/or processor system 102 that can be a part of a controller or workstation 98 having the display 84 and a user interface 106. It will also be understood that the image data is not necessarily first retained in the controller 96, but may also be directly transmitted to the workstation 98. The workstation 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, via the image device controller 96, or adjust the display settings of the display 84. The workstation 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 26 can further include the tracking system including either or both of the electromagnetic (EM) localizer 94 and/or the optical localizer 88. The tracking systems may include a controller and interface portion 110. The controller 110 can be connected to the processor portion 102, which can include a processor included within a computer. The controller acts as a robotic control system. The EM tracking system may include the STEALTHSTATION@ AXIEM™ Navigation System, sold by Medtronic Navigation, Inc. having a place of business in Louisville, Colorado; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON® or S7™ tracking systems having an optical localizer, that may be used as the optical localizer 88, and sold by Medtronic Navigation, Inc. of Louisville, Colorado. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller 110. Also, the tracking devices 62, 66, 54 can generate a field and/or signal that is sensed by the localizer(s) 88, 94.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

According to various embodiments, the navigation system 26 can be used to track the instrument 68 relative to the patient 30. The instrument 68 can be tracked with the tracking system, as discussed above. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a translation map to be generated of the physical location of the instrument 68 relative to the image space of the image data. The translation map allows the tracked position of the instrument 68 to be displayed on the display device 84 relative to the image data 108. A graphical representation **68*i*, also referred to as an icon, can be used to illustrate the location of the instrument 68 relative to the image data 108**.

With continuing reference to FIG. 1, a subject registration system or method can use the tracking device 58. The tracking device 58 may include portions or members that may be trackable, but may also act as or be operable as a fiducial assembly 120. The fiducial assembly 120 can include a clamp or other fixation portion 124 and the imageable fiducial body 122. It is understood, however, that the fiducial assembly 120 may be separate from the tracking device 58. The fixation portion 124 can be provided to fix any appropriate portion, such as a portion of the anatomy. As illustrated in the display 84 of FIG. 1, the fiducial assembly 120 can be interconnected with a portion of a spine 126 such as a spinous process 130. The fixation portion 124 can be interconnected with a spinous process 130 in any appropriate manner. For example, a pin or a screw can be driven into the spinous process 130.

Referring now to FIG. 2A, one process that the end effector assembly 44 may be used for is a drilling process for pedicle screw implantation into a vertebra. However, the teachings also apply to other types of tools. The end effector assembly 44 is a variable stiffness end effector used to guide the tool at a desired position. Previous systems used rigid coupling of the end effector or compliant coupling but do not provide a system capable of providing variable stiffness by switching between compliant coupling and rigid coupling. That is, during a procedure it may be advantageous to be rigid for a portion of the procedure and compliant during other portions such as when vibrations are sensed.

The desired position for the procedure of the effector assembly 44 is located by movement of the robotic arm 40. The variable stiffness end effector 44 is rigidly coupled to the robotic arm 40 during a portion of the procedure. When a drill is used as the tool, it may rotate at a high speed such as over 70000 rpms. Both the robotic arm 40 and the end effector assembly 44 have a resonant or natural frequency. The motion of the tool may cause the end effector assembly 44 to vibrate at a frequency that corresponds to a resonant or natural frequency of the end effector assembly 44, which may be deemed undesirable because it can be felt by the surgeon. Further, the harmonics of the vibration at the robot arm 40 may align with the vibration frequency at the end effector assembly 44 which may cause the rigidly coupled robotic arm to vibrate as well, which may be undesired. The variable stiffness end effector refers to an assembly allowing a tool holder of the end effector 44 (as described below) that absorbs vibration.

A representation of the robotic arm 40 and elbow joint 50 of the effector assembly 44 are illustrated. The effector assembly 44 has the coupling to the arm 40 represented by a spring 210 though which vibration may be coupled. The natural or resonant frequency of the system is the square root of the quotient of the stiffness and mass of the robotic arm. One example of a suitable robotic system is found in U.S. Pat. No. 11,135,035, the disclosure of which is incorporated by reference herein.

Referring now to FIG. 2B, the robot arm 40 is illustrated with the effector assembly 44 thereon. In this example, a vertebra 212 is illustrated. The vertebra is the pivot point 214 of the instrument 68 and the effector assembly 44. Lateral forces are illustrated by the arrow 216. Longitudinal forces are illustrated by the arrow 218 in FIG. 2C. The lateral force 216 is due to the surgeon and the tool to patient reactive force. The forces and deflection are relative to the robotic arm and the patient. The robotic arm motion causes a deviation which may be undesirable but monitored. The patient motion may be monitored or unmonitored. Arm motion and patient motion based on the energy balances at the end of the arm 40 at the effector 44 are described below.

$$\text{Drill Longitudinal Work} = F*d$$

$$\text{Internal Energy} = \Delta U$$

$$\text{Heat} = \Delta Q$$

$$\text{Rotational Energy} = 1/2[I\omega]^2$$

$$\text{Drill Rotational Work} = T*\theta = T*w*t$$

$$\text{Linear Spring Energy} = 1/2[k(\Delta x)]^2$$

$$\text{Rotational Spring Energy} = 1/2[G(\Delta\theta))]^2$$

The work of the rotation by the drill is the product of T, the drill torque, ω, the rotation speed of the drill, and t, the time over which the work is done. The drill longitudinal work is the product of the force, F, of the drill and the distance, d. The rotational spring work uses the spring constant G and the angular distance θ through which the drill travels. The linear spring energy uses the spring constant, k, and the distance in the X direction to determine the spring work. The work also manifests in the energy U and heat Q at the vertebra.

The work may be balanced in an equation summing the work being done at different components. The energy balance at the vertebra 212 of the spine is simplified to be:

$$T*\omega*t+F*d=T*\theta\text{spine}+\Delta\text{U}+\Delta Q$$

where the work of the rotation by the drill is the product of T, the drill torque, w, the rotation speed of the drill, and t, the time over which the work is done. The drill work Z is the product of the force, F, of the drill and the distance, d, and the angular distance Θ through which the drill travels. The work also manifests in the energy U and heat Q at the vertebra.

Because patient rotation and Shanz arm force resistance is zero. The formula for energy balance is simplified above. The lateral forces are due to the surgeon and surgeon tool lateral forces at 216. In this example, the tool slides freely in the arm axially relative to the longitudinal axis 314 of the end effector assembly 44. There are no vertical forces to the arm 40 and there is no rotational torque to the tool insertion device described below.

Figure 2D:
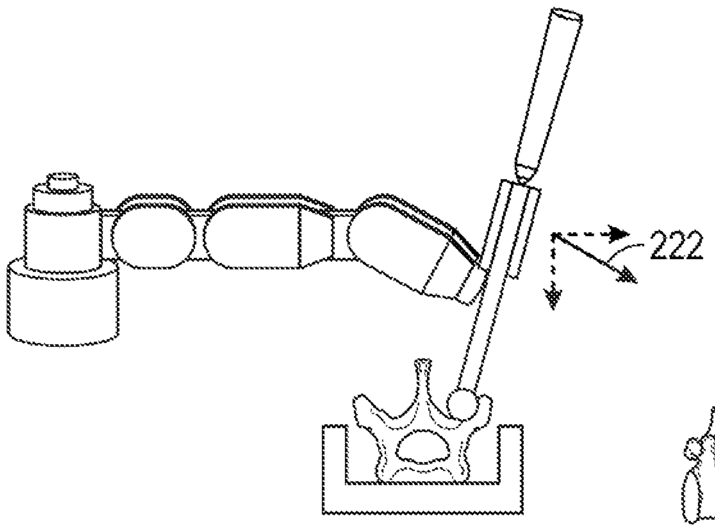
FIGS. 2D and 2E are respective front and side views of a robotic arm having right lateral tilt forces and Shanz forces parallel with the spine.
Figure 2E:
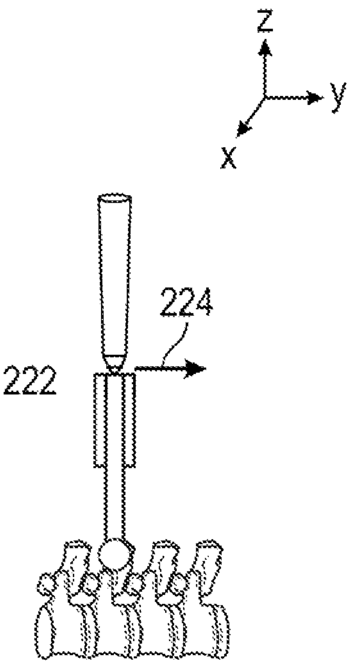

Referring now to FIGS. 2D and 2E, the reactive force 222 and longitudinal force 224 are illustrated. In this example, there is right lateral force and a Shanz force that is parallel with the spine as illustrated in 224. Therefore, the Shanz arm force does not resist lateral forces. In this example, the work balance formula is:

$$T*\omega*t+F*d=T*\theta\text{spine}+\frac{1}{2}kptn(\Delta y)^2+\Delta U+\Delta Q$$

All of the elements are described above except the patient translation which is half of the product of the stiffness spring constant due to the patient's anatomy's deflection under load, kptn, and the square of the lateral distance moved by the patient.

Figure 2F:
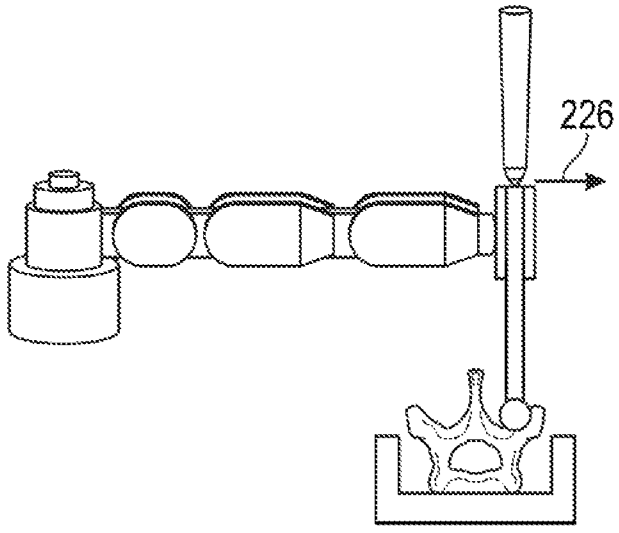
FIGS. 2F and 2G are respective front and side views of a robotic arm having cranial tilt and Shanz forces parallel with the spine.
Figure 2G:
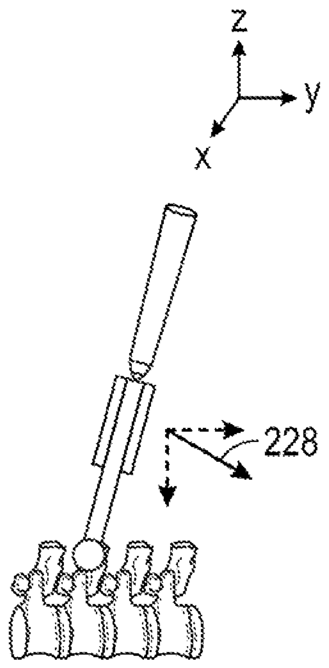

Referring now to FIGS. 2F and 2G, a lateral force 226 is illustrated while a reaction force 228 is illustrated in FIG.

2G. In this example, cranial tilt, a Shanz parallel force is provided relative to the spine and does not resist a compressive force. In this example, the work force equation is the same as that directly above.

Figure 2H:
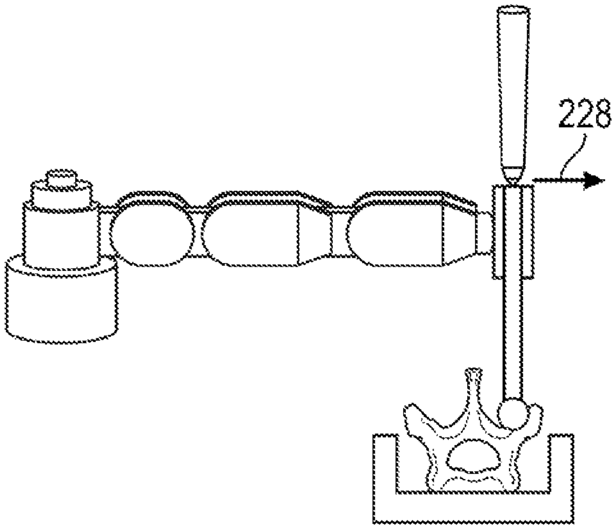
Figure 2I:
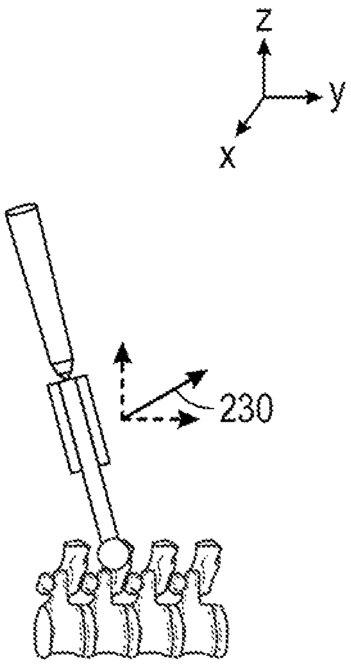

Referring now to FIGS. 2H and 21, in this example, there is the force 228 in a lateral direction and force 230 illustrated in FIG. 21 having an upward or direction away from the vertebra. In this example, a caudal tilt force, a Shanz force is parallel to the spine and resists a tensile force. The work equation is simplified to:

$$T*\omega*t+F*d=T*\theta\text{spine}+\Delta\text{U}+\Delta Q=\frac{1}{2}k(\Delta y)^2$$

Figure 2J:
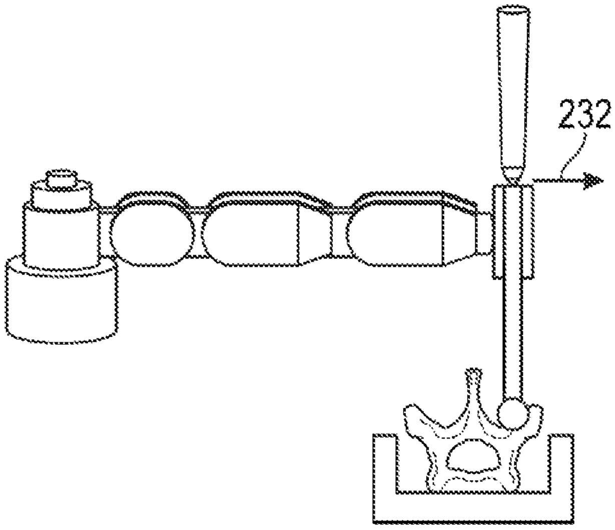
FIGS. 2J and 2K are respective front and side views of a robotic arm having cranial tilt forces and broken Shanz forces parallel with the spine.
Figure 2K:
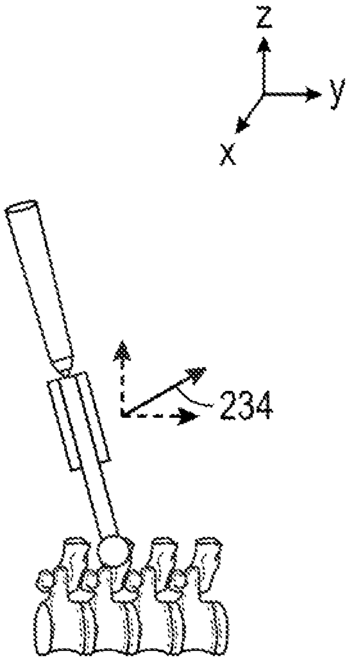

Referring now to FIGS. 2J and 2K, forces 232 and 234 are illustrated. In this example, the forces 232 and 234 correspond to caudal tilt and a broken Shanz arm parallel with the spine. The forces set forth herein simplify to:

$$T*\omega*t+F*d=T*\theta\text{spine}+\frac{1}{2}kptn(\Delta y)^2+\Delta U+\Delta Q$$

Figure 2L:
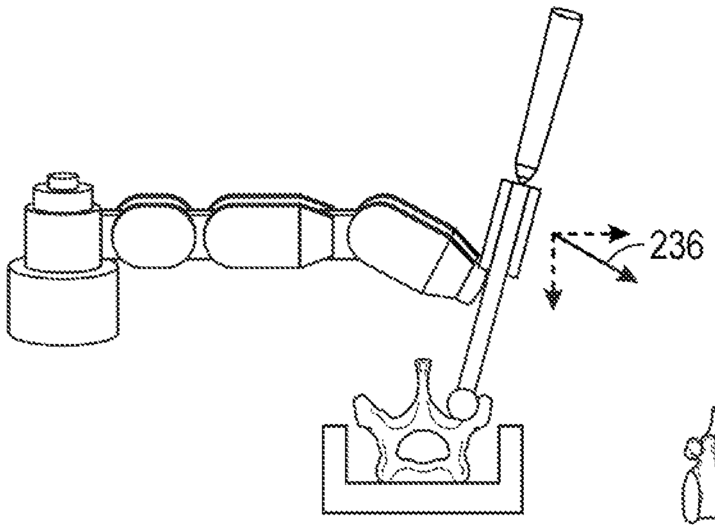
FIGS. 2L and 2M are respective front and side views of a robotic arm having right later tilt forces and Shanz forces perpendicular to the spine.
Figure 2M:
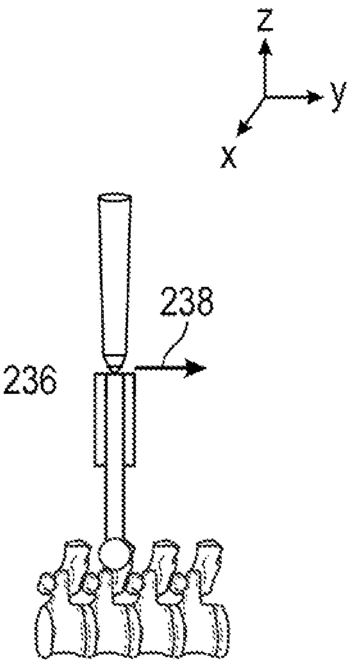

Referring now to FIGS. 2L and 2M, forces 236 and 238 are illustrated and correspond to a right lateral tilt and a Shanz force perpendicular to the spine. The Shanz force does not resist compressive force. The work equation simplifies to:

$$T*\omega*t+F*d=T*\theta\text{spine}+\frac{1}{2}kptn(\Delta x)^2+\Delta U+\Delta Q$$

Figure 2N:
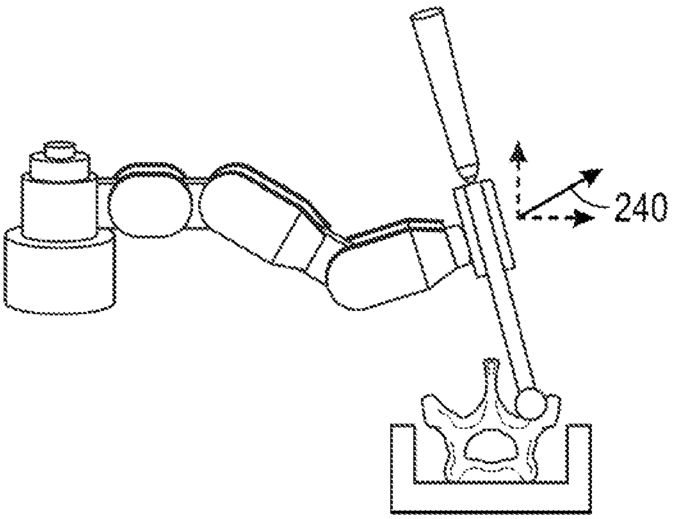
FIGS. 2N and 2O are respective front and side views of a robotic arm having left lateral tilt forces and Shanz forces perpendicular with the spine.
Figure 2O:
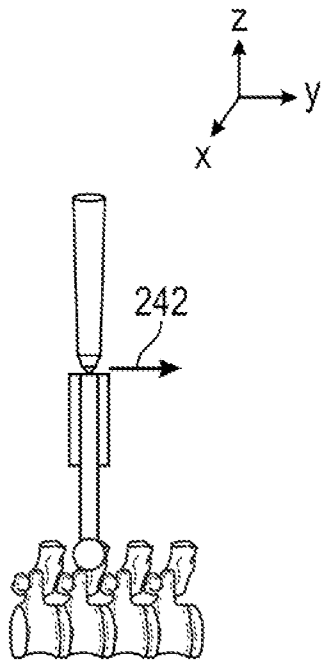

Referring now to FIGS. 2N and 2O, forces 240 and 242 are illustrated. In this example, a left lateral tilt in Shanz force perpendicular to the spine are illustrated. The Shanz arm resists a tensile force. The simplified work equation is set forth as:

$$T*\omega*t+F*d=T*\theta\text{spine}+\Delta\text{U}+\Delta Q+\frac{1}{2}k(\Delta x)^2$$

Figure 2P:
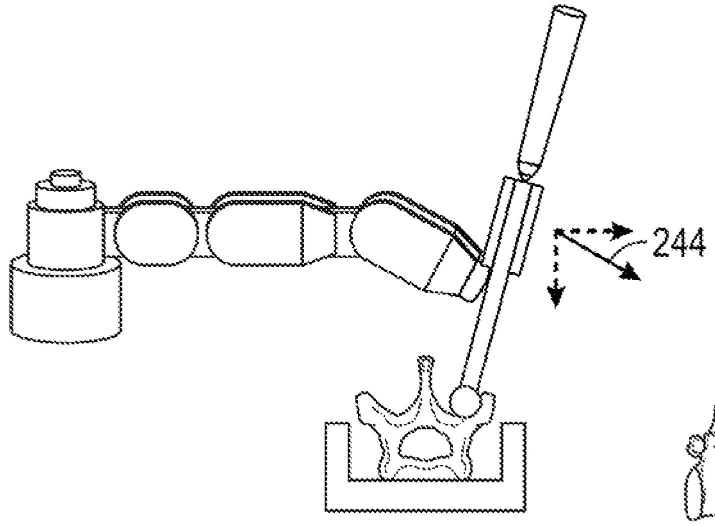
FIGS. 2P and 2Q are respective front and side views of a robotic arm having right lateral forces, Shanz forces parallel with the spine and drill grip surfaces but does not drive into the vertebrae (skiving).
Figure 2Q:
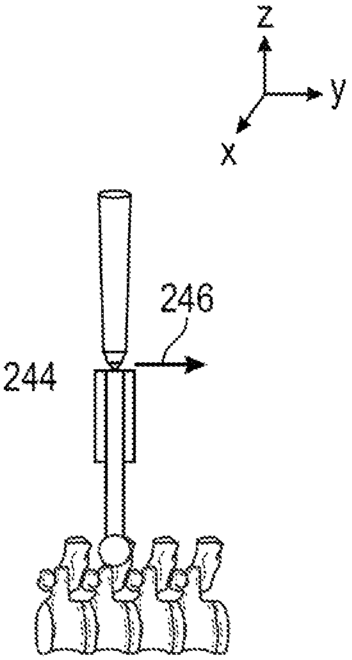

Referring now to FIGS. 2P and 2Q, forces 244 and 246 are illustrated. In this example, a right lateral tilt force and a Shanz force parallel with the spine are illustrated. The Shanz force does not resist lateral force. In this example, the drill grips the surface but does not drive into the vertebra 212. The work equation simplifies in this case to:

$$T*\omega*t=\frac{1}{2}G\ (\Delta\theta ptnt)^2+\frac{1}{2}kptn(\Delta x)^2$$

Figure 3B:
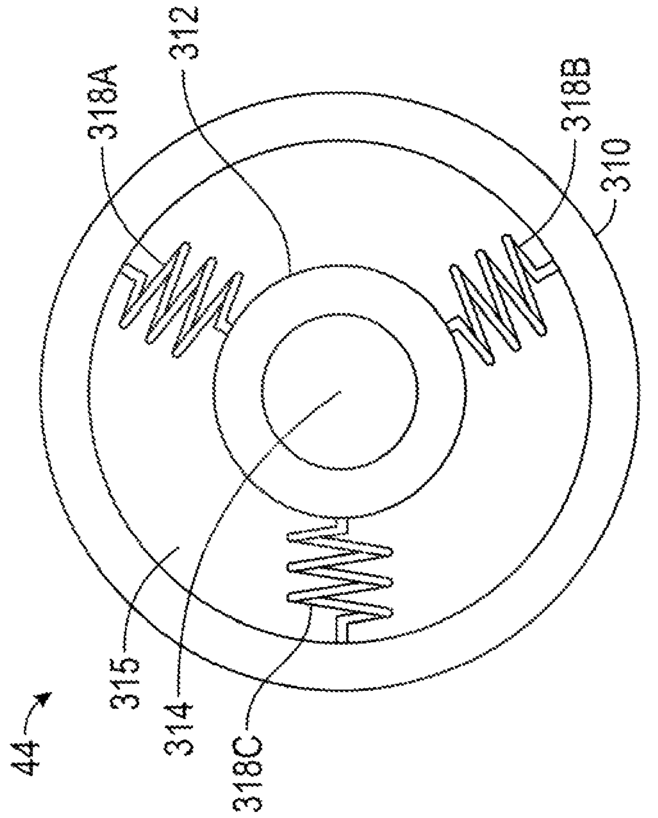
FIG. 3B is the coupler of FIG. 3A in a compliant mode.
Figure 3A:
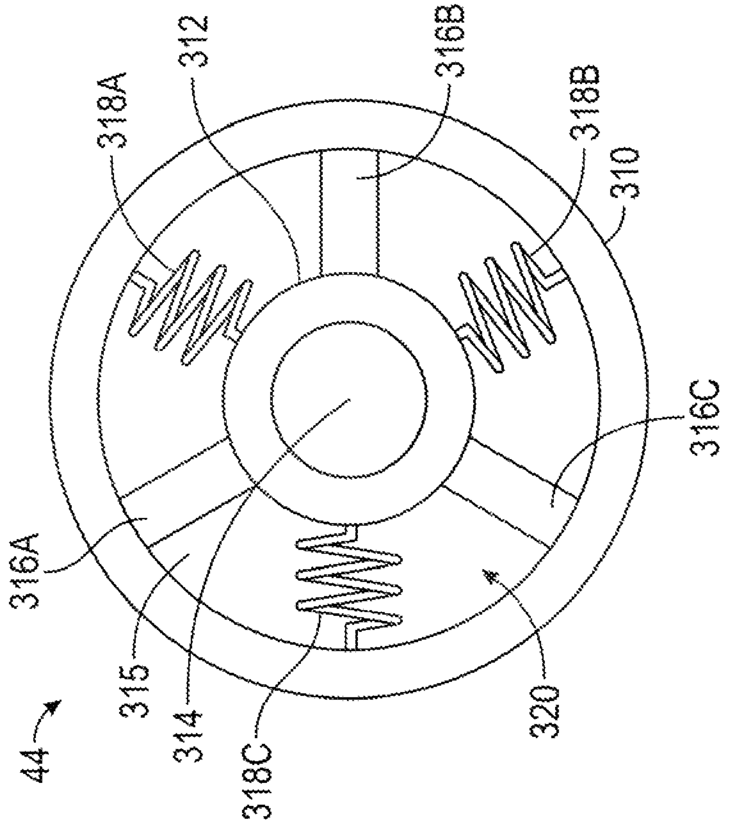
FIG. 3A is a first example of a coupler between an end effector support and a tool insertion device in a rigid mode.

Referring now to FIG. 3A, the end effector assembly 44 is illustrated in a simplified view. The effector assembly 44 is an elongated guide tube as illustrated above in FIGS. 2A-2Q. The end effector assembly 44 has an end effector support 310 and a tool insertion device 312 disposed therein. In this example, the tool insertion device 312 is concentric or coaxial with the end effector support 310 about the longitudinal axis 314 when in rigid mode. In this example, the end effector support 310 and the tool insertion device 312 are tubular and circular in shape and define an annular space 315 therebetween. In FIG. 3A, the end effector support 310 is held rigid to the tool insertion device 312. That is, the tool insertion device 312 is held rigidly inside the end effector support 310.

A rigid coupling mechanism such as a plurality of radially extending pins 316A, 316B and 316C are disposed axially and hold the tool insertion device 312 fixed relative to the end effector support 310. As mentioned above, the forces of a tool being inserted into the tool insertion 312 may have a plurality of forces that are transmitted to the end effector support 310. The end effector support 310 may then transmit the forces or vibrations to the robotic arm 40 illustrated above. The end effector support 310 is affixed rigidly to the robotic arm 40 and therefore the vibrations travel from the effector support 310 to the robotic arm 40. The pins 316A, 316B and 316C are retractably coupled to the end effector support 310 so as to allow compliant coupling.

Referring now to FIGS. 3A and 3B, a compliant mechanism such as springs 318A, 318B and 318C are illustrated between the inner wall of the end effector support 310 and the outer wall of the tool insertion device 312. The springs 318A, 318B and 318C are illustrated as coil springs. However, other types of spring or compliant mechanisms may be used. For example, the compliant mechanisms may include but are not limited to coil springs, leaf springs, torsional springs, compression springs, rounds springs, foam, foam rubber and other compressible material. In FIG. 3A, the springs 318A-318C do not act to rigidly hold the tool insertion device 312 within the end effector support 310. However, when vibrations are sensed at the effector assembly 44, the pins 316A-316C may be retracted or removed so that the end effector support 310 has the tool insertion device 312 rigidly decoupled therefrom. That is, the springs 318A-318C act as the compliant mechanism to allow compliance in the movement of the tool insertion device 312 and to hold the tool insertion device 312 in place. Therefore, the vibrations and forces provided by the tool on the tool insertion device 312 are reduced so as not to be undesirable at the end effector support 310.

In this manner, the amount of forces or vibration from the effector assembly 44 is reduced or eliminated relative to the robot arm 40. In a compliant mode, the tool insertion device 312 moves within and relative to the end effector support 310. The movement may be caused by the vibration of the tool and thus the vibration at the tool insert device 312. The compliant mechanism locally expands and contracts to absorb the vibrations and prevents or reduced the vibration at the end effector support 310. In compliant mode, the tool insertion device 312 may not be concentric relative to the end effector support 310. The tool insertion device 312 is held within the end effector support 310 with the complaint mechanism.

Figure 3C:
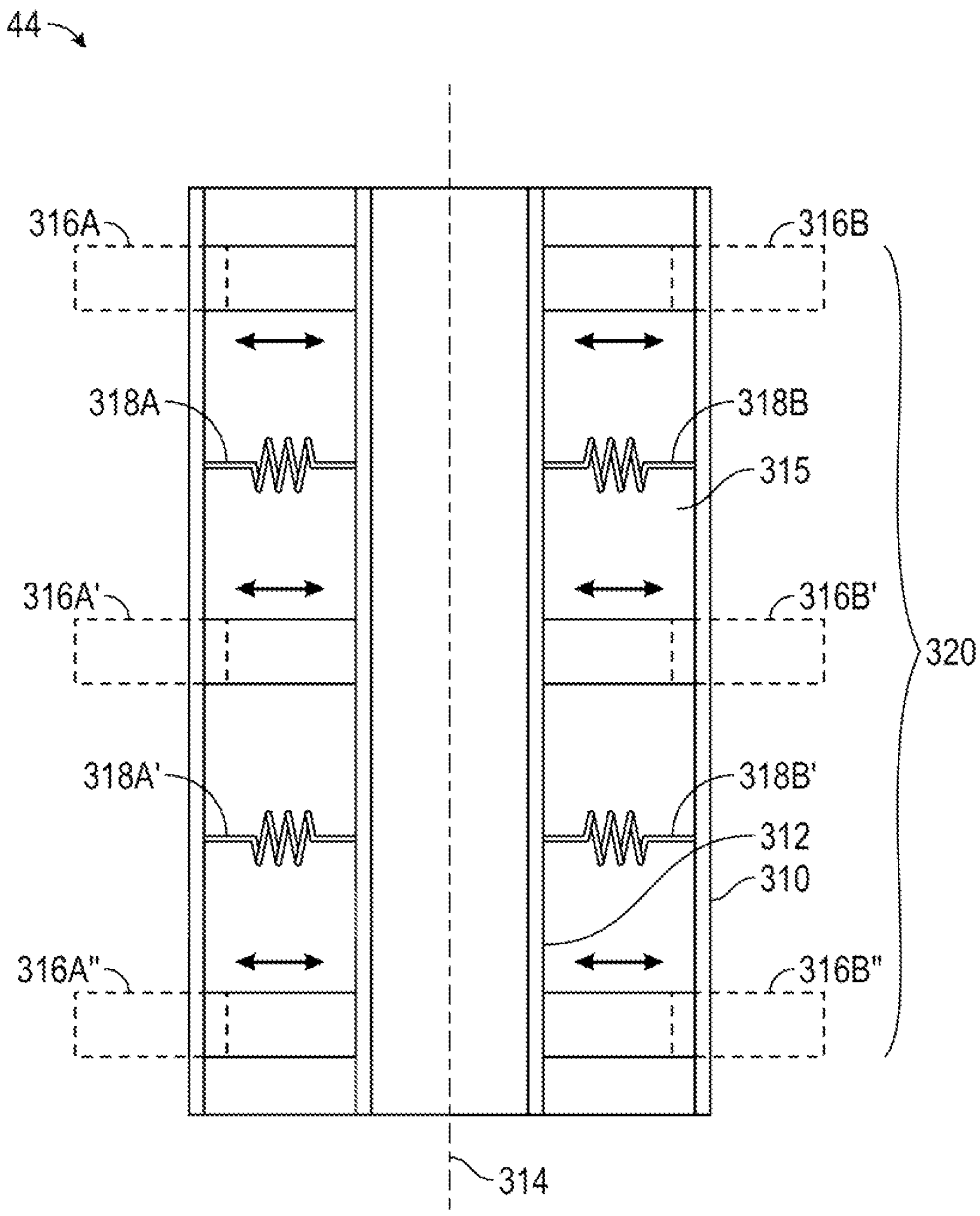
FIG. 3C is a longitudinal cross-sectional view of the end effector assembly of FIGS. 3A and 3B.
Figure 3D:
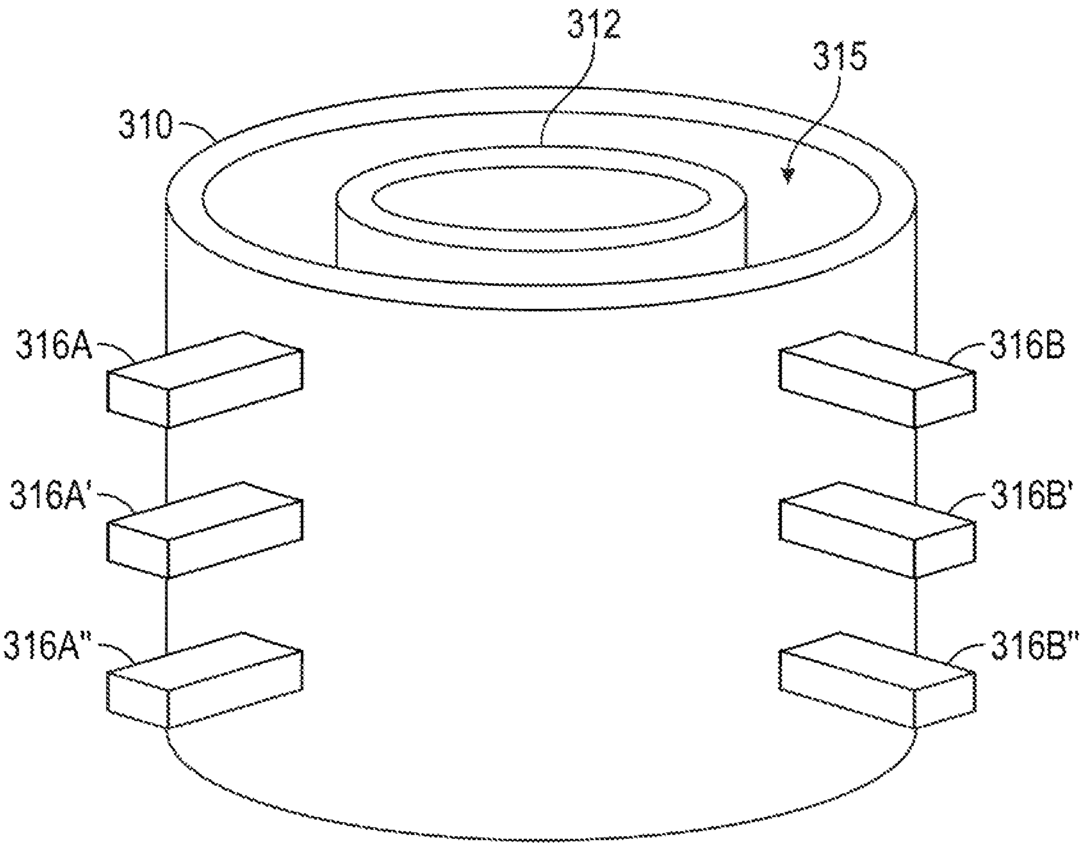
FIG. 3D is a perspective view of effector assembly of FIG. 3C.

Referring now to FIGS. 3C and 3D, a cutaway view of the effector assembly 44 is illustrated. In this example, three sets or levels or rows of axially place support pins 316A-316C are illustrated. That is, a plurality of pins may be required depending upon the length of the effector. The outboard most pins 316A and 316A" be used together with pins 316B-316B". Pins 316C and 316C" are not illustrated in this cutaway view as they are out of view but present behind the tool insertion device 312. In some examples, only pins located near the center of the length of the effector assembly 44 may be used. In this example, pins 316A'-316B' are set forth in the center of the length. The pins 316A-316C'" are illustrated in a rigid mode. However, the dotted lines illustrate where the pins 316A-316C" may be in a compliant mode or retracted mode. The pins in FIGS. 3A-3C together with the actuator such as a solenoid, motor, (now shown in FIGS. 3A-3C) may be referred to as a coupler 320.

In FIG. 3C, two sets of springs 318A-318C and 318A'-318B' are illustrated. Various numbers of sets of springs may be implemented. For example, only one set of springs may be provided or a spaced apart set of springs may be provided depending upon the system requires and the forces required to be overcome. Of course, if foam or foam rubber is used the foam or foam rubber may continuously surround the inner device may be pieces spaced apart within the annular space 315.

Figure 4B:
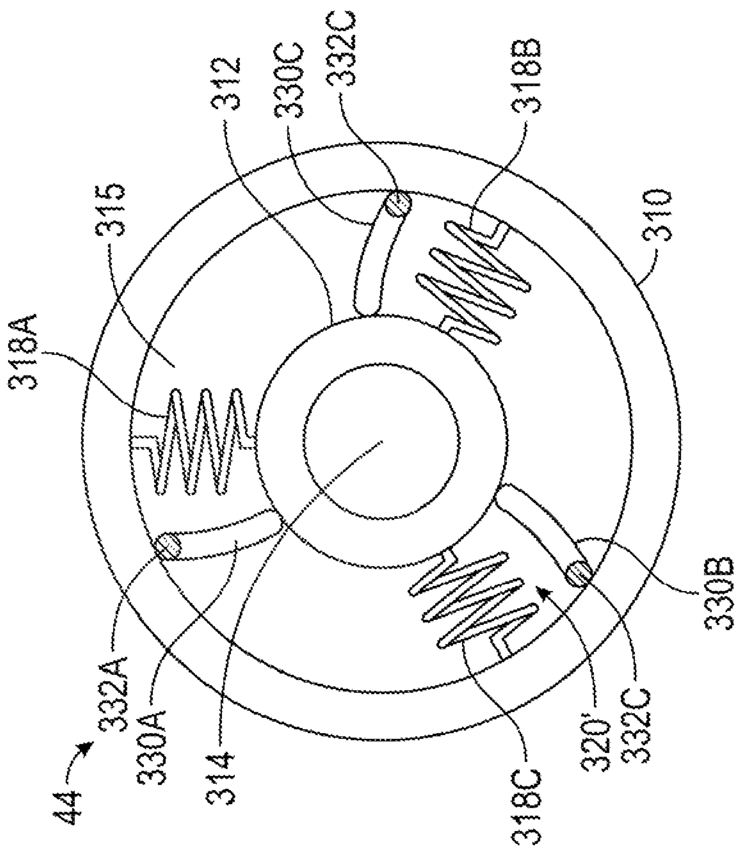
FIG. 4B is the effector assembly of FIG. 4A in a rigid mode.
Figure 4A:
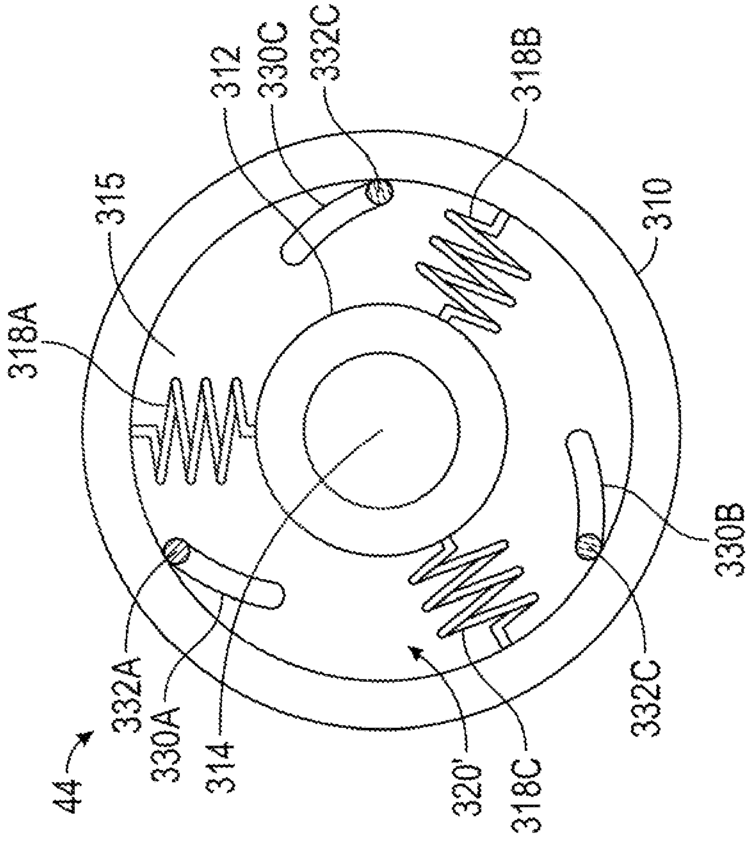
FIG. 4A is a second example of a coupler in a compliant mode.

Referring now to FIGS. 4A and 4B, a second example of a coupler 320' is illustrated. In this example, the coupler 320' is a rigid coupling mechanism illustrated as a plurality of cams 330A, 330B and 330C. The cams 330A-330C have motors that are used to rotate the cams into and out of the positions illustrated in FIGS. 4A and 4B. The cams 330A, 330B and 330C are actuators that are used to change modes. In the mode illustrated in FIG. 4A, the tool insertion device 312 is compliant and therefore can move relative to the end effector support 310 as resisted by the springs. In FIG. 4B, the cams 330A-330C are rotated into engagement with the tool insertion device 312 by the motors 332A-332C. The motors 332A and cams 330A may be referred to later as an actuator.

As illustrated in FIG. 3C, sets of cams 330A-330C and springs 318A-318C may be disposed in different positions within the longitudinal length of the effector 44.

Figure 5:
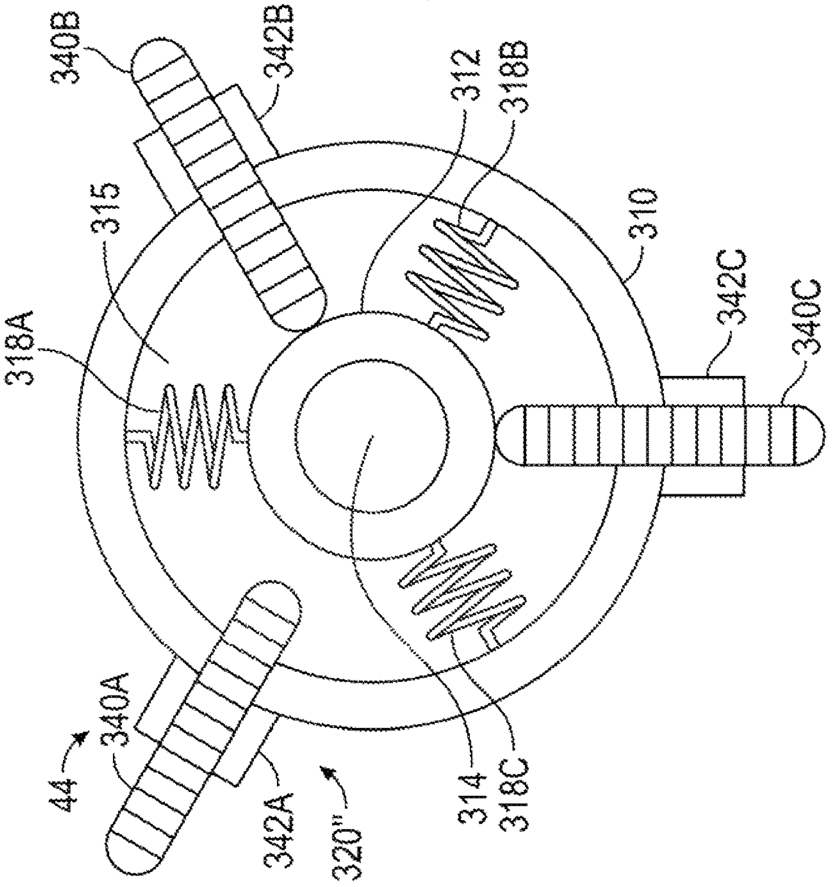
FIG. 5 is a cross-sectional view of a third example of a coupler of an end effector assembly.

Referring now to FIG. 5, another example of a coupler 320" that acts as the rigid coupling mechanism is illustrated. In this example, the coupler 320" comprises a plurality of fasteners such as screws 340A-340C. The screws 340A-340C extend through the wall of the end effector support 310. The coupler 320" also includes a plurality of motors 342A, 342B and 342C that are coupled to respective screws 340A-340C The motors may be a stepper motor or a solenoid. It should be that the screw 340A is illustrated in a retracted position so that effector 44 is in a compliant mode. The screws 340B and 340C are illustrated in the rigid mode. When desired, the screws 340A-340B are rotated from one mode to another mode. As mentioned above, the screws 340A-340C may be retracted to reduce transmission of vibration and therefore enter a compliant mode. Although screw 340A is shown retracted, all three screws 340A-340C may be moved simultaneously during a procedure.

Figure 6:
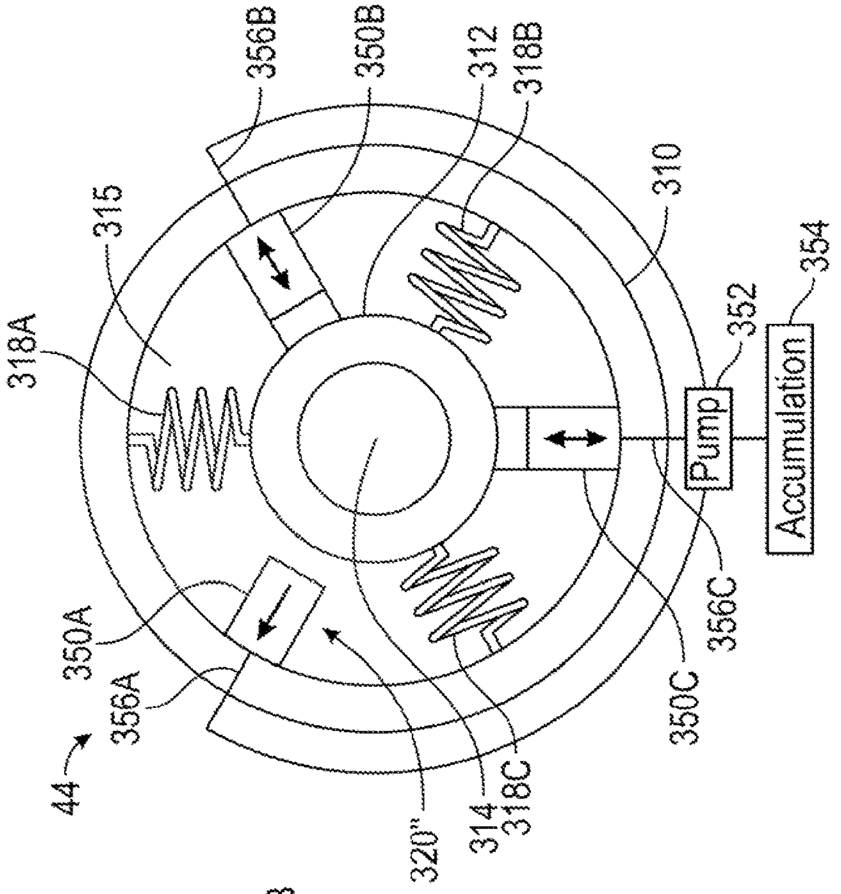
FIG. 6 is a cross-sectional view of a pneumatic coupler, two of which are in a rigid position and one in a compliant position.

Referring now to FIG. 6, another example of a coupler 320" is illustrated. The coupler 320'" acts as a rigid coupling mechanism that has a plurality of retractable pneumatic cylinders 350A-350C. In a similar manner to that illustrated in FIG. 5, the pneumatic cylinders 350A-350C may operate simultaneously. However, in this example, the cylinder 350A is shown in a retracted or compliant position. The cylinders 350B and 350C are illustrated in a rigid position. The cylinders 350A-350B have a pump that provide pressure or air to the pneumatic cylinders 350A-350C. An accumulator 354 provides a reservoir for air to be provided or within from the cylinders 350A-350C. It should be noted that the pneumatic cylinders may also be replaced by hydraulic cylinders with hydraulic fluid therein. In this example, passages 356A, 356B and 356C are provided through the wall forming the end effector support 310. The pump 352 and the pneumatic cylinders 350A-350C form the actuator for switching between a compliant mode and a rigid mode as described above.

The example of FIG. 6 may be configured with many groups of compliant mechanisms such as the springs 318A-318C and groups of rigid mechanisms such as the pneumatic cylinders 350A-350C at different positions along the length of the effector assembly similar to that set forth in FIG. 3C.

Figure 7B:
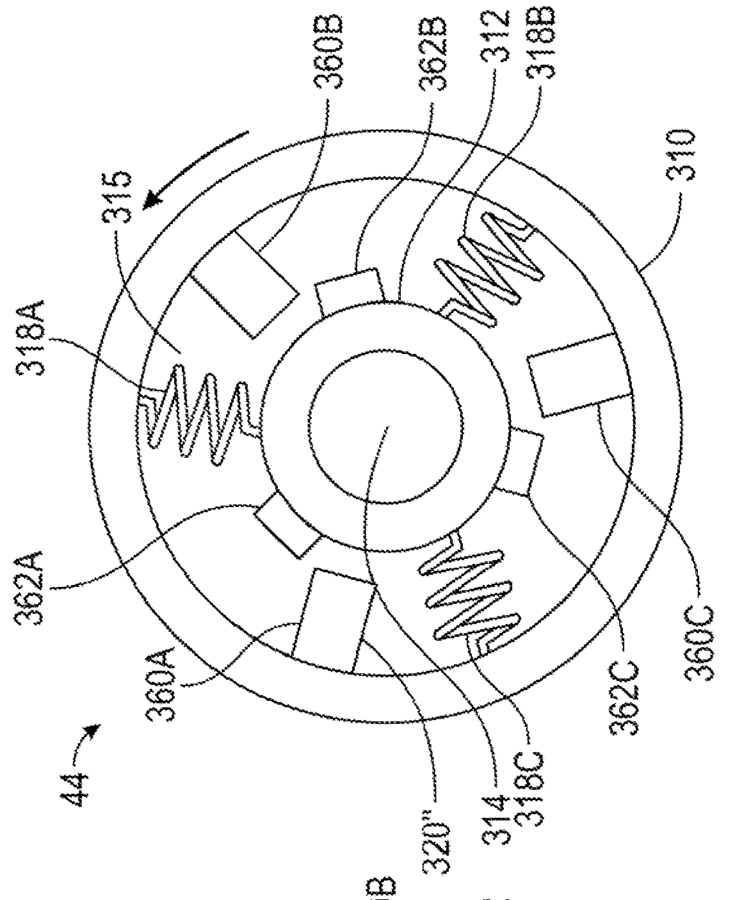
FIG. 7B is a cross-sectional view of the end effector assembly of FIG. 7*a* in a compliant mode.
Figure 7A:
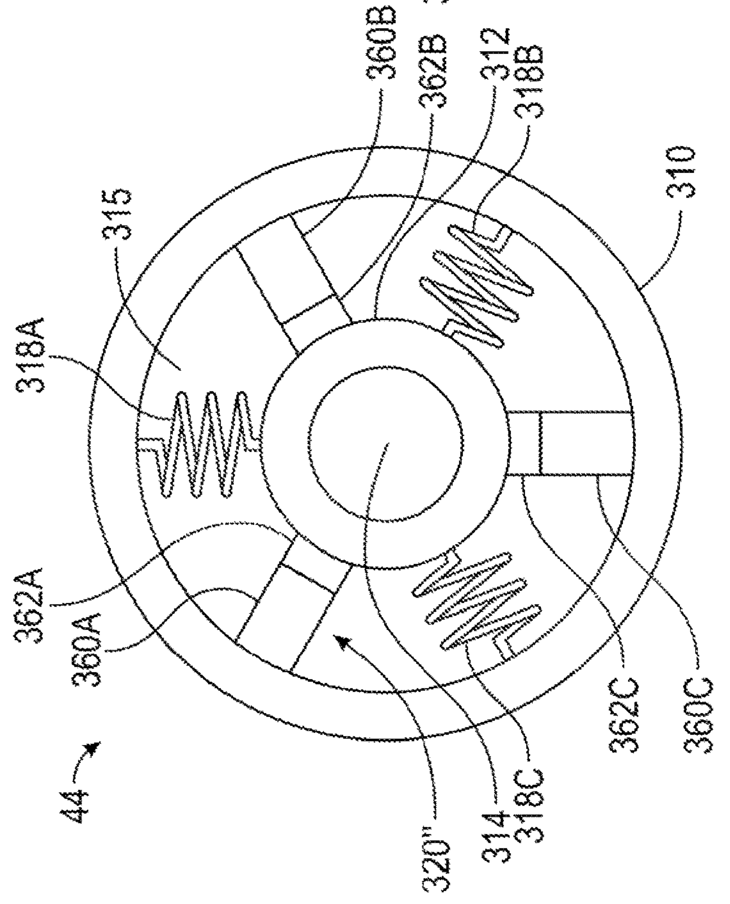
FIG. 7A is another example of a coupler of an end effector in a rigid mode.
Figure 7C:
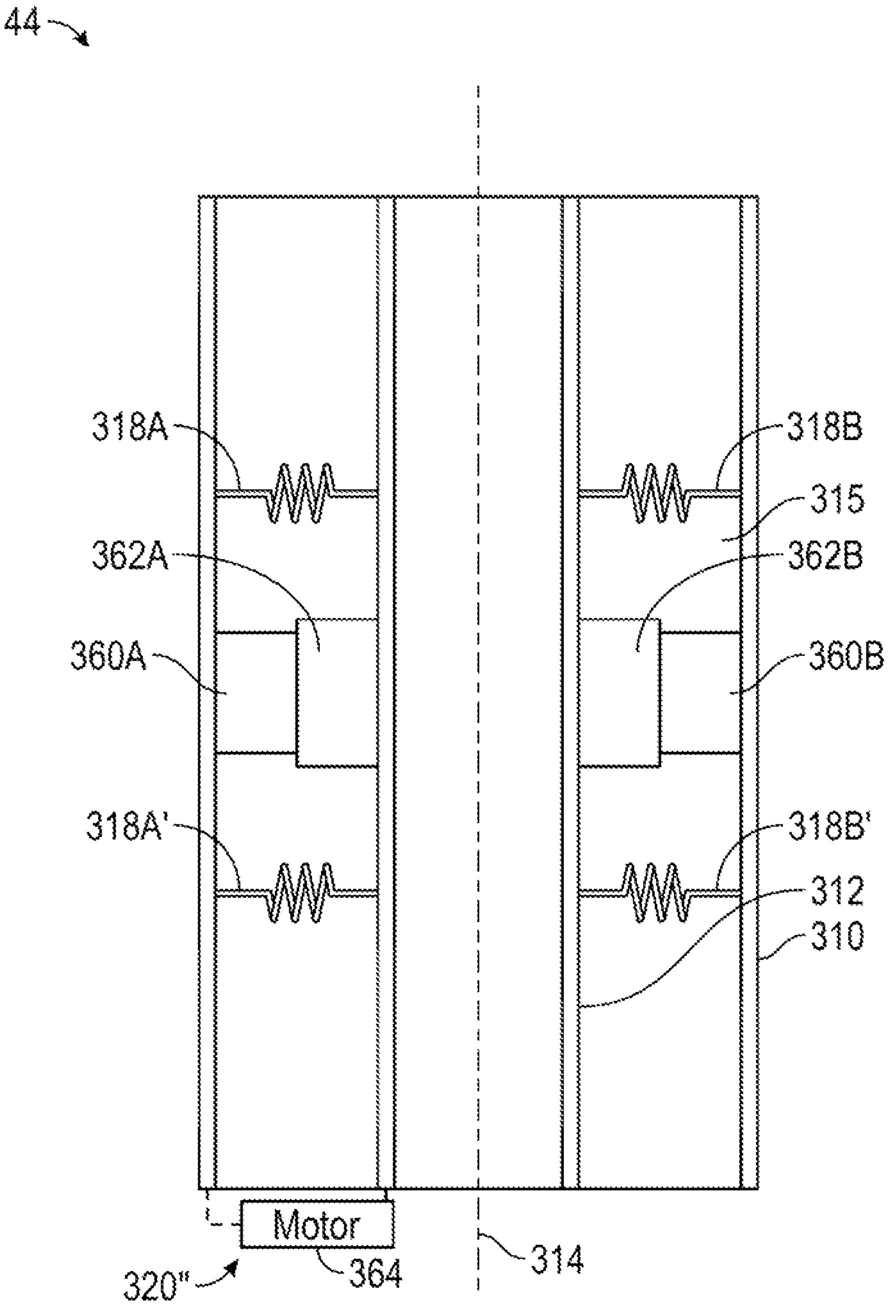
FIG. 7C is a longitudinal cross-sectional view of the end effector assembly of FIGS. 7A and 7B.

Referring now to FIG. 7A-7C, an effector 44 in a fourth example of a rigid coupling mechanism, a coupler $\mathbf{320}^{IV}$, is set forth. In this example, a first set of stops 360A, 360B and 360C extend axially from the end effector support 310. A second plurality of stops 362A, 362B and 362C extend axially from the tool insertion device 312. In a rigid position as illustrated in FIG. 7A, the stops 360A-360C line up respectively with respect to the stops 362A-362C. The stops form a similar configuration to the pins illustrated in FIG. 3A. However, in FIG. 7B, the stops 360A-360C are misaligned with the stops 362A-362C. That is, in FIG. 7B, a compliant mode is entered wherein the springs 318A-318C hold the tool insertion device 312 within the end effector support 310.

In FIG. 7C, the tool insertion device 312 is illustrated relative to the end effector support 310. In this example, the stops 360A are engaged with stop 362A and stop 360B is engaged with stop 362B. In this example, two sets of springs 318A, 318B and 318A' and 318B' are illustrated. In this example, a motor 364 is used as part of the actuator. The motor 364 rotates the relative position of the tool insertion device 312 and the end effector support 310. A small rotation may be provided by the motor 364 to the tool insertion device 312 or the end effector support 310 so that the sets of stops are misaligned when needed. Of course, the motor 364 may realign the stops when the rigid mode is to be entered. The mode acts as part of the coupler $\mathbf{320}^{IV}$.

As illustrated best in FIG. 7B, the springs 318A-318C flex but are compliant enough to allow the position of the tool insertion device to move and prevent the transmission of vibration or movement to the end effector support 310.

Figure 8:
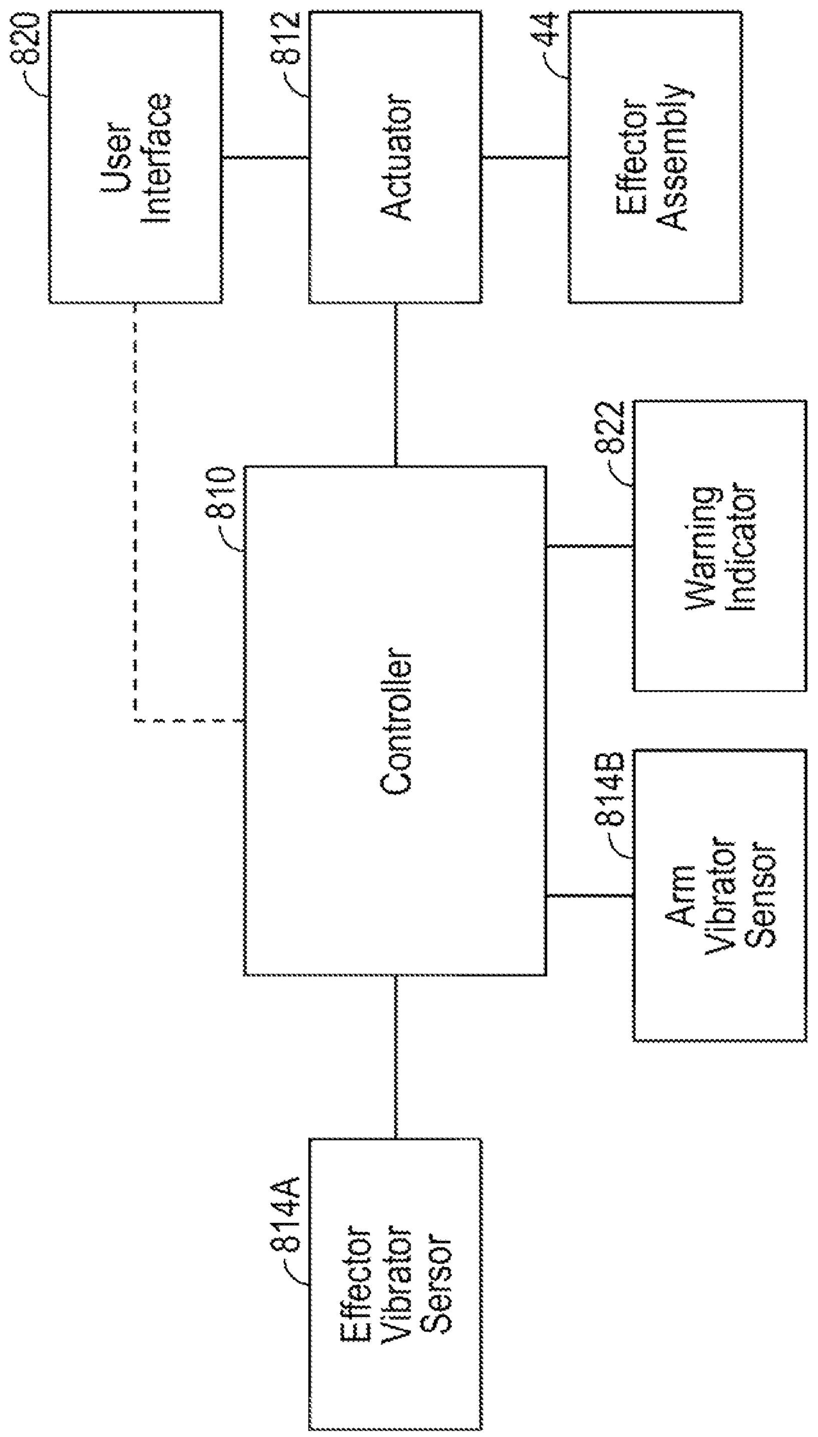
FIG. 8 is a block diagrammatic view of a system for controlling an end effector assembly into a compliant mode and a rigid mode.

Referring now to FIG. 8, the system may be automatically controlled by a controller 810 or manually controlled by the surgeon. The system may be stand-alone or incorporated into a controller such as the controller 110 described above. The controller 810 may be microprocessor-based and is programmed to perform various steps including controlling an actuator 812 in response to a vibration from an effector vibration sensor 814A or a robotic arm vibration sensor 814B. The controller 810 may be one of the controllers described above such as the controller 110 which acts as the robotic control system. That is, the vibration sensor 814A may be positioned on the outside, inside or end of the effector assembly 44 or the tool insertion device. The vibration sensor 814B may be fixed to one of the segments of the robot arm 40. Upon sensing a natural frequency vibration at one of the vibration sensors 814A, 814B (with an amplitude above a predetermined threshold), the controller 810 may automatically control one of the actuators 812 illustrated in FIGS. 3-7 should the vibrations reach a threshold level. The actuator 812 may move the mechanical coupling mechanism relative to the effector assembly so that the end effector support 310 is rigidly disengaged with the tool insertion device 312 to cease the rigid mode and enter a compliant mode. The compliant device allows the tool insertion device 312 to maintain a position within the end effector support 310. The vibration sensors 814A, 814B provide vibration signals to the controller 810. When the vibration ceases after the compliant mode is entered (amplitude below a predetermined threshold), the vibration sensor 814 may allow the controller 810 to control re-engagement of the rigid coupling mechanism in the rigid mode. That is, the actuator 812 may hold the tool insertion device relative to the end effector support 310.

The system may also be used in a manual mode. A user interface 820 may be located external to the effector assembly 44 to initiate manually decoupling of the end effector support 310 from the tool insertion device 312. A foot pedal, button, dial or the like, may be used by the surgeon as the user interface 820. Upon sensing vibration, the effector assembly 44 is switched from the tool insertion device 312 being coupled in the rigid mode to a compliant mode. The surgeon may do this by feel or in response to a warning indicator 822 such as a buzzer or a light. That is, when a vibration in the natural frequency greater than a predetermined amplitude is sensed at the robotic arm or the effector assembly, a warning signal (light and/or sound), may be generated. The warning signal may be generated at the display 84 of the workstation 98. After the vibration or movement ceases, the user interface 820 may be used to re-engage the actuator 812 to re-enter a rigid mode. Of course, the controller 810 may be part of the surgery system and integrated in the controller 110.

Figure 9:
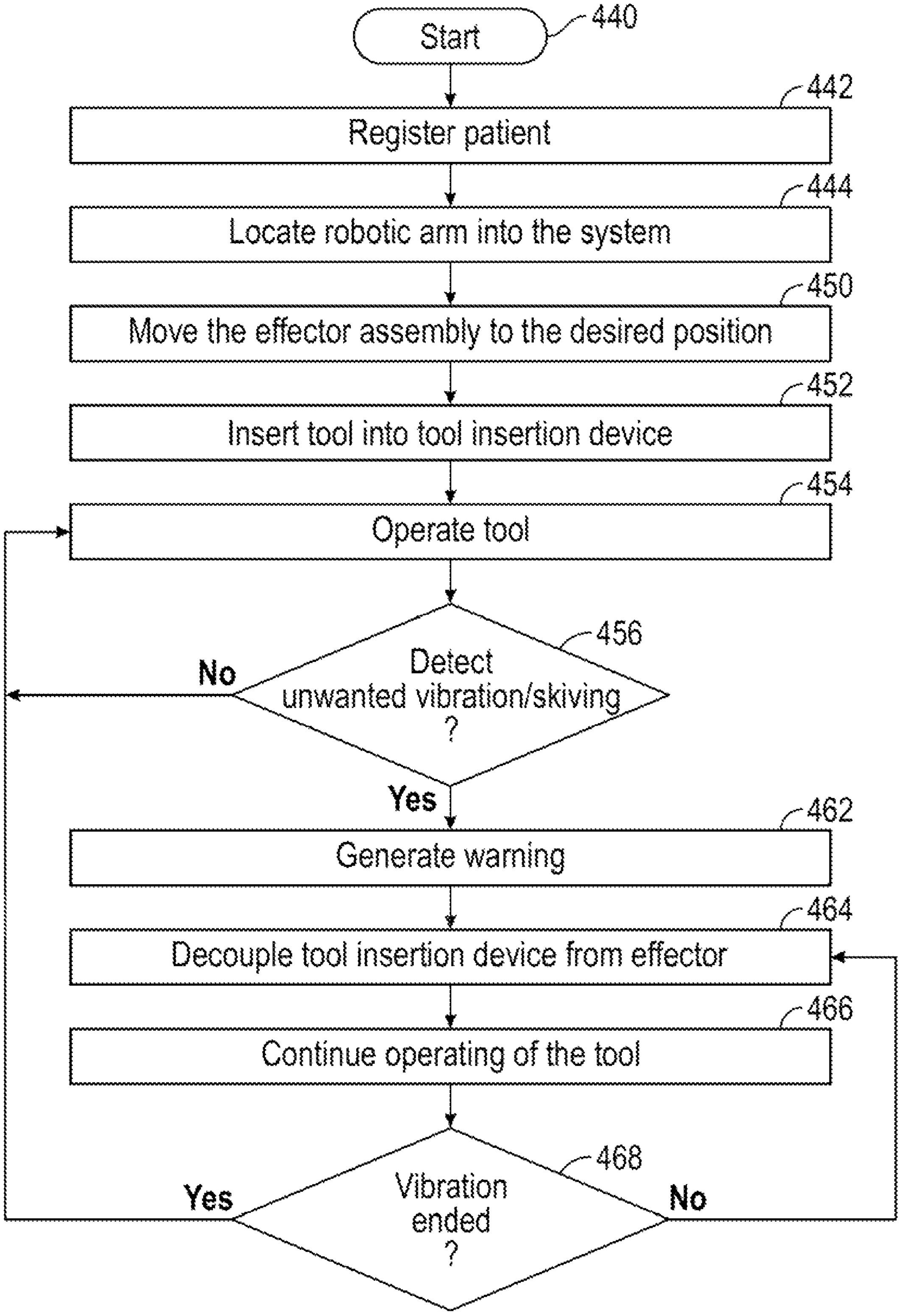
FIG. 9 is a flowchart of a method for performing a procedure using the end effector assembly in a rigid or compliant mode.

With reference to FIG. 9, a process 430 is illustrated. The process 430 is used to switch modes from a rigid mode to a compliant mode at the effector 44 and may be included in a guided surgery procedure.

The process 430 may start in start Block 440.

In Block 442. the patient position is registered into the system. The robotic arm in Block 444 is also registered and located into the robotic surgery system.

In Block 450, the robotic system 20 may then move the effector assembly 44 in a manner based on known anatomy. As illustrated above, in FIGS. 2A-2Q, the effector assembly 44 may be moved into various positions relative to the patient. The robot arm 40 is used to move the variable stiffness effector assembly 44 to the desired position that can be tracked by the navigation system. In one example, the end effector support 310 and the tool insertion device 2312 are in a rigid mode.

In Block 452, the tool is inserted into the tool insertion device. In Block 454, the tool, such as a drill, is activated or operated.

In Block 456, the vibration sensors are monitors to determine whether unwanted drill vibration or skiving is detected. As mentioned above, the detection of vibration or the vibration associated with skiving may be detected at a vibration sensor that detects a certain frequency or a vibration that is above a certain amplitude threshold. The surgeon may also detect the unwanted vibration through visual, audible or a tactile feeling of the effector assembly 44, the robotic arm or the tool.

In response to the vibrations from the vibration sensor 814A or 814B, or the user interface 820, Block 462 may generate a warning signal and the tool insertion device 312 is automatically rigidly decoupled from the effector support 310. That is, the tool insertion device is placed into a compliant mode in Block 464. The surgeon may then continue operating the tool within the tool insertion device in block 466.

In Block 468, if the vibration is not present, the tool insertion device remains decoupled from the effector in Block 464. In Block 468, if the vibration has ended, Block 454 continues the process of operating the tool.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a processor (also referred to as a processor module) that may include a special purpose computer (i.e., created by configuring a processor) and/or a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, JAVAR, ASP, JAVASCRIPT®, HTML5, Ada, ASP (active server pages), Perl, Scala, Erlang, Ruby, FLASH®, VISUAL BASIC®, Lua, or PYTHON®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor, processor module, module or 'controller' may be used interchangeably herein (unless specifically noted otherwise) and each may be replaced with the term 'circuit.' Any of these terms may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processor module" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A variable stiffness end effector assembly for a medical robotic guidance system comprising:

an end effector support;

a tool insertion device disposed within and spaced apart from the end effector support; and a coupler coupling the tool insertion device within the end effector support, the coupler comprising:

a rigid coupling mechanism configured to rigidly couple the tool insertion device within the end effector support in a first mode, and a compliant device configured to compliantly couple the tool insertion device within the end effector support in a second mode, wherein engagement of the rigid coupling mechanism in the first mode prevents engagement of the compliant device, and engagement of the compliant device in the second mode prevents engagement of the rigid coupling mechanism.

2. The variable stiffness end effector assembly of claim 1 wherein the end effector support comprises a first elongated tube and the tool insertion device comprises a second elongated tube, wherein the first elongated tube is coaxial with the second elongated tube in the first mode.

3. The variable stiffness end effector assembly of claim 1 wherein the compliant device comprises at least one of a plurality of springs, foam, and foam rubber.

4. The variable stiffness end effector assembly of claim 1 wherein the coupler comprises a plurality of pins retractably disposed between the end effector support and the tool insertion device.

5. The variable stiffness end effector assembly of claim 1 wherein the rigid coupling mechanism comprises a plurality of cams retractably coupled between the end effector support and the tool insertion device.

6. The variable stiffness end effector assembly of claim 5 wherein the plurality of cams is coupled to a motor.

7. The variable stiffness end effector assembly of claim 1 wherein the rigid coupling mechanism comprises a first plurality of stops coupled to the end effector support and a second plurality of stops coupled to the tool insertion device, wherein in the first mode the first plurality of stops are aligned with the second plurality of stops, and in the second mode the first plurality of stops align with the first plurality of stops.

8. The variable stiffness end effector assembly of claim 7 wherein the first plurality of stops extends axially from the end effector support and the second plurality of stops extend axially from the tool insertion device.

9. The variable stiffness end effector assembly of claim 7 wherein the end effector support is rotated relative to the tool insertion device.

10. The variable stiffness end effector assembly of claim 1 wherein the rigid coupling mechanism comprises a plurality of fasteners retractably coupled through the end effector support and is axially retractable relative to the tool insertion device.

11. The variable stiffness end effector assembly of claim 10 wherein the plurality of fasteners are screws coupled to a motor.

12. The variable stiffness end effector assembly of claim 1 wherein the rigid coupling mechanism comprises a plurality of pneumatic cylinders retractably coupled to the end effector support and axially retractable relative to the tool insertion device, the pneumatic cylinder coupled to a pump.

13. The variable stiffness end effector assembly of claim 1 further comprising a vibration sensor coupled to the end effector support, the tool insertion device or a robotic arm, the vibration sensor generating a vibration signal corresponding to a vibration of the end effector support, the tool insertion device or the robotic arm, and a controller coupled to the vibration sensor, the controller automatically switching the coupler from the first mode to the second mode in response to the vibration signal.

14. The variable stiffness end effector assembly of claim 1 further comprising a vibration sensor coupled to the end effector support, the tool insertion device or a robotic arm, the vibration sensor generating a vibration signal corresponding to a vibration of the end effector support, the tool insertion device or the robotic arm, and a controller coupled to the vibration sensor, the controller generating a warning signal in response to the vibration signal, the coupler manually decoupling the end effector support from the tool insertion device.

15. The variable stiffness end effector assembly of claim 1 wherein the coupler comprises a plurality of rigid coupling mechanisms and a plurality of compliant devices disposed at different positions along a length of the end effector support.

16. A system, comprising:

a robotic arm having a variable stiffness end effector assembly comprising a tool insertion device disposed within an end effector support and coupled thereto with a coupler;

the coupler comprising;

a rigid coupling mechanism configured to rigidly couple the tool insertion device within the end effector support in a first mode, and a compliant device configured to compliantly couple the tool insertion device within the end effector support in a second mode, wherein engagement of the rigid coupling mechanism in the first mode prevents engagement of the compliant device, and engagement of the compliant device in the second mode prevents engagement of the rigid coupling mechanism;

a robotic control system configured to control movement of the end effector assembly; and an input system configured to receive input from a user and send a signal to the robotic control system to move the end effector support relative to a subject.

17. The system of claim 16 wherein the end effector support and the tool insertion device are elongated.

18. The system of claim 16 wherein the end effector support comprises a first elongated tube and the tool insertion device comprises a second elongated tube.

19. The system of claim 18 wherein the first elongated tube is coaxial with the second elongated tube in the first mode.

20. The system of claim 16 wherein the compliant device comprises a plurality of springs.

21. The system of claim 16 wherein the rigid coupling mechanism comprises a plurality of pins retractably disposed between the end effector support and the tool insertion device.

22. The system of claim 16 wherein the rigid coupling mechanism comprises a plurality of cams retractably coupled between the end effector support and the tool insertion device.

23. The system of claim 22 wherein the plurality of cams is coupled to a motor.

24. The system of claim 16 wherein the rigid coupling mechanism comprises a first plurality of stops coupled to the end effector support and a second plurality of stops coupled to the tool insertion device, wherein in the first mode the first plurality of stops are aligned with the second plurality of stops, and in the second mode the first plurality of stops align with the second plurality of stops.

25. The system of claim 24 wherein the first plurality of stops extends axially from the end effector support and the second plurality of stops extend axially from the tool insertion device.

26. The system of claim 24 wherein the end effector support is rotated relative to the tool insertion device.

27. The system of claim 16 wherein the rigid coupling mechanism comprises a plurality of fasteners retractably coupled through the end effector support and is axially retractable relative to the tool insertion device.

28. The system of claim 27 wherein the plurality of fasteners are screws coupled to a motor.

29. The system of claim 16 wherein the rigid coupling mechanism comprises a plurality of pneumatic cylinders retractably coupled to the end effector support and axially retractable relative to the tool insertion device, the pneumatic cylinder coupled to a pump.

30. The system of claim 16 further comprising a vibration sensor coupled to the end effector support, the tool insertion device or a robotic arm, the vibration sensor generating a vibration signal corresponding to a vibration of the end effector support, the tool insertion device or the robotic arm, and a controller coupled to the vibration sensor, the controller automatically switching the coupler from the first mode to the second mode in response to the vibration signal.

31. The system of claim 16 further comprising a vibration sensor coupled to the end effector support, the tool insertion device or a robotic arm, said vibration sensor generating a vibration signal corresponding to a vibration of the end effector support, the tool insertion device or the robotic arm, and a controller coupled to the vibration sensor, the controller generating a warning signal in response to the vibration signal, the coupler manually decoupling the end effector support from the tool insertion device.

32. The system of claim 16 wherein the coupler comprises a plurality of rigid coupling mechanisms and a plurality of compliant devices disposed at different positions along a length of the end effector support.

33. The system of claim 16 further comprising a user interface configured to enable manually switching of the coupler between the first mode and the second mode.

* * * * *